United States Patent [19]

Umezawa et al.

[11] Patent Number: 4,474,764

[45] Date of Patent: Oct. 2, 1984

[54] 3-AMINO-2-HYDROXY-4-PHENYL-BUTANOIC ACID DERIVATIVES AND PHARMACEUTICAL COMPOSITION CONTAINING THE SAME

[75] Inventors: Hamao Umezawa; Tomio Takeuchi, both of Tokyo; Takaaki Aoyagi, Fujisawa; Mitsugu Hachisu, Tokyo; Kenji Kawamura, Ohiso; Shunzo Fukatsu; Yasuharu Sekizawa, both of Tokyo, all of Japan

[73] Assignee: Zaidan Hojin Biseibutsu Kagaku Kenkyu Kai, Japan

[21] Appl. No.: 425,875

[22] Filed: Sep. 28, 1982

[30] Foreign Application Priority Data

Oct. 13, 1981 [JP] Japan ................... 56-161994

[51] Int. Cl.$^3$ .................. A61K 37/00; C07C 103/52; C07C 149/43; C07C 101/00; C07C 101/30; C07C 101/32; C07C 149/40; C07C 123/00; C07C 101/72

[52] U.S. Cl. .................. 424/177; 260/112.5 R; 560/16; 560/35; 560/39; 560/40; 562/426; 562/440; 562/444; 562/445; 562/448

[58] Field of Search .............. 560/16, 35, 39, 40; 562/426, 440, 444, 445, 448; 260/112.5 R; 424/177

[56] References Cited

U.S. PATENT DOCUMENTS 4,052,449 10/1977 Umezawa et al. ........... 260/112.5 R
4,185,156 1/1980 Umezawa et al. .................. 424/319
4,189,604 2/1980 Umezawa et al. .................. 424/319
4,395,402 7/1983 Umezawa et al. .................. 424/177

FOREIGN PATENT DOCUMENTS 1540019 7/1979 United Kingdom .

OTHER PUBLICATIONS

Chem. Abstr. vol. 93, 204275y, (1980).
Chem. Abstr. vol. 91, (1979), 57545q.
Chem. Abstr. vol. 93, (1980), 72280j.
Chem. Abstr. vol. 97, (1982), 44350w.
Chem. Abstr. vol. 97, (1982), 306g.
J. of Med. Chem., (1977) 20, pp. 510-515.

Primary Examiner—Delbert R. Phillips
Attorney, Agent, or Firm—Larson and Taylor

[57] ABSTRACT

New 3-N-acyl derivatives of 3-amino-2-hydroxy-4-phenylbutanoic acid are provided, which exhibit analgesic activity and are affective to enhance the morphine analgesia.

9 Claims, No Drawings

3-AMINO-2-HYDROXY-4-PHENYLBUTANOIC ACID DERIVATIVES AND PHARMACEUTICAL COMPOSITION CONTAINING THE SAME

SUMMARY OF THE INVENTION

This invention relates to new compounds having analgesic activity and more particularly to new 3-amino-2-hydroxy-4-phenylbutanoic acid derivatives and pharmaceutically acceptable salts thereof. This invention also relates to a new analgesic agent comprising the new compounds as the active ingredient.

BACKGROUND OF THE INVENTION

It is known that enkephalin or endorphine as the analgesic peptide exists in the brain of mammalian animals and particularly enkephalin is existing at a high level in the vesicles of the nervous cells at the nerve ending of the nerve fibre in the brain, and also that enkephalinase is co-existing in the same areas as those where the enkephalin is found. Besides, the possibility that enkephalin functions as neurotransmitters in the central nervous system of mammalian animals is suggested in the "Nature" Vol. 276, pages 523 to 526 (1980).

Furthermore, it has been revealed that acupuncture analgesia is mediated through release of the analgesic peptides such as enkephalin in the brain when the effectiveness of acupuncture analgesia was examined by measuring tail-flick latency of rats while the contents of the analgesic peptides in the brain were determined (see the Japanese medicinal journal "Showa Igakukai Zasshi" Vol. 39, No. 5, pages 537 to 542 (1979). It is also reported that the analgesic activity of morphine is relying on that morphine plays a role to cause enkephalin to be released in the nervous system (see the "Life Science" No. 25, pages 53 to 60 (1979)).

We have taken the above facts into consideration and we take it that generally, an inhibitor against enkephalinase will show an analgesic activity when it is used alone and it is expected that the inhibitor against enkephalinase will be highly effective for eliminating or minimizing the pain of such patients who feel chronic pain owing to a low level of enkephaline in the brain. In view of the disclosure in the "Showa Igakukai Zasshi" Vol. 39, No. 5, pages 543 to 550 (1979), it is also expected that an enkephalinase-inhibitor will be useful as an aid for enhancing the acupuncture analgesia and morphine analgesia, and that such enkephalinase-inhibitor, even alone, will be effective to change the acupuncture-ineffective patients into the acupuncture-effective patients.

In an attempt to provide a new analgesic agent, therefore, we extensively researched on the inhibitory activity of many known compounds against enkephalinase, the enzyme of degrading enkephalin. As a result, we previously found that 3-amino-2-hydroxy-4-phenylbutanoic acid and some related compounds thereof have the enkephalinase-inhibiting activity in vitro and, when tested in animals, exhibit the analgesic activity in vivo. Based on these previous findings, we devised an invention which relates to an analgesic agent comprising as the active ingredient (2S,3R)-3-amino-2-hydroxy-4-phenylbutanoic acid (abbreviated as AHPA), its amide, its methyl ester, (2R,3R)-3-amino-2-hydroxy-4-phenyl-1-butanol or a dipeptide compound represented either by a formula

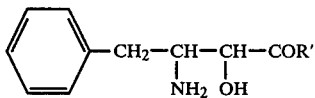

wherein R' is selected from D-leucine residue, D-glutamic acid residue, D-alanine residue, D-arginine residue, D-methionine residue, L-methionine residue, β-alanine residue, D-asparatic acid residue and glycine residue, or by a formula

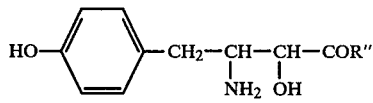

wherein R" is selected from D-leucine residue, L-leucine residue and D-phenylalanine residue (see Japanese patent application No. 131583/1980; U.S. patent application Ser. No. 303,938; U.K. patent application No. 8128604).

The compounds as mentioned above have such a moiety in their chemical structure which is common to that of bestatin, namely (2S,3R)-3-amino-2-hydroxy-4-phenylbutanoyl-(S)-leucine (see U.S. Pat. Nos. 4,029,547 and 4,189,604), and hence they may be said to be bestatin-related compounds in brief.

In a further development of our study, we have now succeeded to synthetize a number of new 3-amino-2-hydroxy-4-phenylbutanoic acid derivatives of a kind different from the above-mentioned known bestatin-related compounds. For the screening purpose, we have tested these new derivative compounds for their activity inhibitory to enkephalinase, the enzyme of degrading the enkephalin. As a result of our screening test, we have now found that amongst the new compounds now synthetized by us which are active as the inhibitor of enkephalinase, the new compounds of the general formula (1) shown below exhibit a significant analgesic activity in animal tests. Thus, we have reached this invention.

DETAILED DESCRIPTION OF THIS INVENTION

According to a first aspect of this invention, therefore, there is provided as the new compound a 3-amino-2-hydroxy-4-phenylbutanoic acid derivative represented by a general formula:

$$R_1-\underset{}{\bigcirc}-CH_2-\overset{*}{C}H-\overset{*}{C}H-COR_3 \quad (1)$$
$$\qquad\qquad\qquad\quad | \quad |$$
$$\qquad\qquad\qquad NHR_2 \; OH$$

wherein $R_1$ is a hydrogen atom or a hydroxyl group; $R_2$ is an N-substituted or unsubstituted α-amino acid residue, a dipeptide residue or a tripeptide residue represented by the formula $$R_4NH-Y-CO(-NH-X-CO)_m$$

where X is an α-amino acid residue which is obtained as a skeletal moiety of the α-amino acid molecule by removing the amino and carboxyl groups from the α-position of the α-amino acid molecule, Y is an α-amino acid residue obtained as a skeletal moiety of an α-amino acid molecule by removing the amino and carboxyl groups from the α-position of an α-amino acid which may be the same as or different from the α-amino acid for X, n is zero or an integer of 1 to 2, and $R_4$ is a hydrogen atom, an alkanoyl group of 2~7 carbon atoms or an alkyl group of 1~4 carbon atoms; or $R_2$ is 4-amino-2-hydroxybutanoyl group or 3-amino-2-hydroxy-4-phenylbutanoyl group; $R_3$ is a hydroxyl group or a lower alkoxyl group of 1~6 carbon atoms; and an asterisk * denotes that the carbon atoms to which the asterisk is attaching may take the R-configuration or the S-configuration or a combination thereof, or a pharmaceutically acceptable salt of said 3-amino-2-hydroxy-2-phenylbutanoic acid derivative of the formula (1).

According to an embodiment of the first aspect of this invention, there is provided an N-acyl 3-amino-2-hydroxy-4-phenylbutanoic acid represented by the formula:

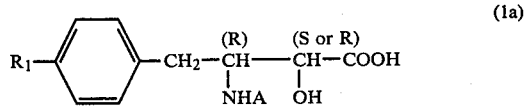
(1a)

wherein $R_1$ is a hydrogen atom or a hydroxyl group; and A is a glycyl group, an N-acetylglycyl group, a methylglycyl group, an R-alanyl group, an R-phenylalanyl group, an N-formyl-R-alanyl group, an R-leucyl group, an S-leucyl group, a glycylglycyl group, an N-acetylglycylglycyl group, an S-tyrosylglycylglycyl group, a 4-amino-(2S)-2-hydroxybutanoyl group or a (2S,3R)-3-amino-2-hydroxy-4-phenylbutanoyl group, or a pharmaceutically acceptable alkyl ester or a pharmaceutically acceptable salt thereof.

Particular examples of the new compounds of the formula (1) or (1a) as above are listed in the following table:

TABLE 1

| Compound No. | Compound Names (Abbreviation) |
|---|---|
| 1 | (2S,3R)-3-N—glycylamino-2-hydroxy-4-phenylbutanoic acid (abbreviated as Gly-AHPA) |
| 2 | (2S,3R)-3-N—glycylamino-2-hydroxy-4-phenylbutanoic acid methyl ester hydrochloride (abbreviated as Gly-AHPA OMe.HCl) |
| 3 | (2S,3R)-3-N—(N'—acetylglycyl)amino-2-hydroxy-4-phenylbutanoic acid methyl ester (abbreviated as N—Ac-Gly-AHPA OMe) |
| 4 | (2S,3R)-3-N—glycylglycylamino-2-hydroxy-4-phenylbutanoic acid (abbreviated as GlyGly-AHPA) |
| 5 | (2S,3R)-3-N—glycylglycylamino-2-hydroxy-4-phenylbutanoic acid methyl ester hydrochloride (abbreviated as GlyGly-AHPA OMe.HCl) |
| 6 | (2S,3R)-3-N—(N'—acetylglycylglycyl)amino-2-hydroxy-4-phenylbutanoic acid (abbreviated as N—Ac-GlyGly-AHPA) |
| 7 | (2S,3R)-3-N—(N'—methylglycyl)amino-2-hydroxy-4-phenylbutanoic acid (abbreviated as Sar-AHPA) |
| 8 | (2S,3R)-3-N—(S)—leucylamino-2-hydroxy-4-phenylbutanoic acid (abbreviated as L-Leu-AHPA) |
| 9 | (2S,3R)-3-N—(R)-leucylamino-2-hydroxy-4-phenylbutanoic acid (abbreviated as D-Leu-AHPA) |
| 10 | (2S,3R)-3-N—(R)-phenylalanylamino-2-hydroxy-4-phenylbutanoic acid (abbreviated as D-Phe-AHPA) |
| 11 | (2S,3R)-3-N—[4'-amino-(2'S)—2'-hydroxybutanoyl]amino-2-hydroxy-4-phenylbutanoic acid (abbreviated as HABA-AHPA) |
| 12 | (2S,3R)-3-N—[(2'S,3'R)-3'-amino-2'-hydroxy-4'-phenylbutanoyl]amino-2-hydroxy-4-phenylbutanoic acid (abbreviated as AHPA-AHPA) |

TABLE 1-continued

| Compound No. | Compound Names (Abbreviation) |
|---|---|
| 13 | (2S,3R)-3-N—(N'—acetylglycylglycyl)amino-2-hydroxy-4-phenylbutanoic acid sodium salt abbreviated as N—Ac-GlyGly-AHPA.Na) |
| 14 | (2S,3R)-3-N—(R)-alanylamino-2-hydroxy-4-phenylbutanoic acid (abbreviated as D-Ala-AHPA) |
| 15 | (2S,3R)-3-N—(N'—formyl-(R)-alanyl)amino-2-hydroxy-4-phenylbutanoic acid sodium salt (abbreviated as N—For-D-Ala-AHPA.Na) |
| 16 | (2R,3S)—3-N—(S)—tyrosylglycylglycylamino-2-hydroxy-4-phenylbutanoic acid (abbreviated as TyrGlyGly-(2R,3S)—AHPA) |
| 17 | (2S,3R)-3-N—(R)-phenylalanylamino-2-hydroxy-4-p-hydroxy-phenylbutanoic acid (abbreviated as D-Phe-p-OH-AHPA) |
| 18 | (2R,3R)-3-N—(R)-leucylamino-2-hydroxy-4-phenylbutanoic acid (abbreviated as D-Leu-(2R,3R)—AHPA) |

Amongst the compounds listed in Table 1 above, the Compound Nos. 6, 10 and 17 are preferred in this invention.

In general, the new compounds of the general formula (1) above may be deemed as an N-acyl derivative of 3-amino-2-hydroxy-4-phenylbutanoic acid (AHPA). When the group $R_2$ which is bonding to the 3-amino group of the 3-amino-2-hydroxy-4-phenylbutanoic acid is represented by the formula $$R_4NH—Y—CO(-NH—X—CO)_n \qquad (2)$$

the moiety —NH—X—CO— which is present within the group $R_2$ may be derived from an α-amino acid such as glycine, alanine, phenylalanine, leucine, isoleucine, arginine and the like, and hence the group —X— may be the residual, sketetal moiety of said α-amino acid which is obtained by removing both the α-amino and α-carboxyl groups from said α-amino acids. These amino acids may be either in the D-form or in the L-form.

Similarly, the moiety $R_4NH—Y—CO—$ where $R_4$ is a hydrogen atom may be derived from an α-amino acid such as glycine, alanine, phenylalanine, tyrosine, arginine, leucine, isoleucine, sarcosine (namely, N-methylglycine) and the like, and hence the group —Y— may be the residual, skeletal moiety of said α-amino acid which is obtained by removing both the α-amino and α-carboxyl groups from the α-amino acid.

Accordingly, the moiety —NH—X—CO— or the moiety —NH—Y—CO— which is present in the molecule of the α-amino acid of the formula (1) may be chosen from the following:

| | |
|---|---|
| Glycine residue: | —NH—CH$_2$—CO— |
| Alanine residue: | —NH—CH(CH$_3$)—CO— |
| Phenylalanine residue: | —NH—CH—CO—<br>　　　　　│<br>　　　　　CH$_2$<br>　　　　　│<br>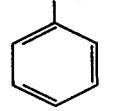 |

-continued

Tyrosine residue:

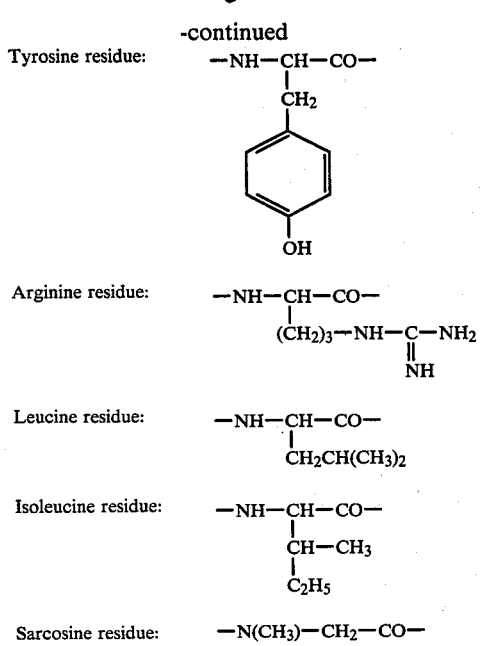

Arginine residue: —NH—CH—CO—
  |
  (CH₂)₃—NH—C—NH₂
       ‖
       NH

Leucine residue: —NH—CH—CO—
  |
  CH₂CH(CH₃)₂

Isoleucine residue: —NH—CH—CO—
  |
  CH—CH₃
  |
  C₂H₅

Sarcosine residue: —N(CH₃)—CH₂—CO—

With the new compound of the general formula (1), the group $R_4$ may be a hydrogen atom or an alkyl group of 1~4 carbon atoms such as methyl or an alkanoyl group of 2~4 carbon atoms such as acetyl and propionyl. It may add that the group $R_2$ may also be an acyl group derived from 4-amino-2-hydroxybutanoic acid (hereinafter sometime abbreviated as HABA) or 3-amino-2-hydroxy-4-phenylbutanoic acid (hereinafter sometime abbreviated as AHPA).

When the new compound of the general formula (1) is such one where the group $R_3$ denotes the hydroxyl group, the whole compound of the formula (1) is in the form of a free carboxylic acid. When the new compound of the formula (1) is such one where the group $R_3$ is an alkoxyl group, the whole compound of the formula (1) is in the form of carboxylic acid alkyl ester (a carboxylate). The group $R_3$ may be an alkoxyl group of 1~6 carbon atoms such as methoxyl, ethoxyl and the like.

The methods for the production of the new compound of the general formula (1) are now described. Generally, the new compound of the formula (1) according to this invention may be produced by condensing the 3-amino group of 3-amino-2-hydroxy-4-phenylbutanoic acid (AHPA) or 3-amino-2-hydroxy-4-p-hydroxyphenylbutanoic acid (hereinafter sometimes abbreviated as p-hydroxy-AHPA) (including various steric isomers of these acids), or a carboxyl-protected derivative thereof, that is, a carboxylic acid of the general formula (3):

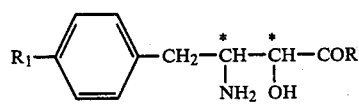

(3)

wherein $R_1$ is a hydrogen atom or a hydroxyl group, and R is a hydroxyl group or a carboxyl-protecting group, for example, an alkoxyl group, and the asterisk * represents that the carbon atoms to which the asterisk is attaching take the R-configuration or the S-configuration or a combination thereof, either with an α-amino acid, a dipeptide or tripeptide of the general formula (4):

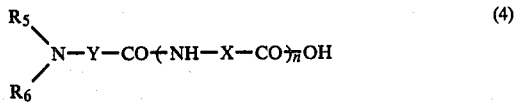

(4)

wherein X, Y and n are as defined above; and either $R_5$ and $R_6$ are each a hydrogen atom, or $R_5$ is an alkyl group or a lower alkanoyl group (which may be the same as the aforesaid $R_4$ group) or another amino-protecting group and $R_6$ is a hydrogen atom, or with AHPA or HABA or an N-protected derivative thereof in a manner known per se in the conventional synthesis of peptides, and then, if required, removing the protective groups (R, $R_5$) from the resultant condensation product by a known deprotection technique.

The reaction of condensing the compound of the general formula (3) with the compound of the general formula (4) or with AHPA or HABA may be performed at a temperature of −20° C. to 25° C. in a known manner according to the carbodiimide method using dicyclohexyl-carbodiimide as the condensation agent; according to the active ester method using e.g. hydroxysuccinimide ester, according to the active amide method using imidazole and the like; according to the active azide method using e.g. hydrazine; or according to the mixed acid anhydride method using ethyl chloroformate. The organic solvent in which the condensation is conducted may be those employed for the conventional synthesis of peptides and includes, for example, ethers such as tetrahydrofuran and dioxane; esters such as ethyl acetate; ketones such as acetone; halogenated hydrocarbons such as methylene chloride; amides such as dimethylformamide; and nitriles such as acetonitrile. The reaction of condensing the compound of the formula (3) with a dipeptide or tripeptide compound of the formula (4) is effected according to so-called "fragment condensation" method, but the production of the compound of the general formula (1) may be achieved according to so-called "stepwise chain elongation" method where the compound of the formula (3) is condensed with an α-amino acid in a first step and then further with another α-amino acid in a second step, and so on. Even when the "stepwise chain elongation" method is employed, the condensation reaction involved may be effected in a known manner. The functional groups such as amino group, hydroxyl group, carboxyl group and guanidyl group which are possibly present in the α-amino acid or peptide compound of the formula (4) and which should not participate in the condensation reaction may, if necessary, have been protected by a known suitable protective group. For instance, the amino group may be protected by a known amino-protecting group such as an alkoxyl-carbonyl group, e.g., t-butoxycarbonyl and an aralkyloxycarbonyl group e.g. benzyloxycarbonyl. The carboxyl group may be protected by a known carboxyl-protecting group such as benzyl. The removal of the residual amino-protecting group from the condensation product as obtained may be done by a deprotecting technique known in the chemistry of peptides. For instance, the amino-protecting aralkyloxycarbonyl group, especially benzyloxycarbonyl group may be removed by catalytic hydrogenolysis in the presence of a palladium catalyst, and the alkoxycarbonyl group such as tert-butoxycarbonyl group may be removed by mild acidolysis with hydrogen bromide in acetic acid, with trifluoroacetic acid or with hydrogen chloride in an organic solvent such as dioxane, tetrahydrofuran and ethyl acetate. Alkaline hydrolysis is also effective for the deprotection, depending on the nature of the protective group present in the resultant condensation product.

When the compound of the general formula (1) as obtained from the condensation process as above is yielded in the form of a free carboxylic acid ($R_3$=OH), it may be converted into a corresponding alkyl ester ($R_3$=alkoxyl), if desired, by reacting with a lower alkanol such as methanol in the presence of an acid catalyst. Such a compound of the formula (1) where $R_4$ is an alkyl group or an alkanoyl group may also be produced by alkylating a corresponding compound of the formula (1) where $R_4$ is a hydrogen atom, with a usual alkylation reagent such as alkyl chloride, or by acylating the amino group of the corresponding compound of the formula (1) where $R_4$ is a hydrogen atom, with a usual acylation reagent such as acetyl chloride in a known manner. For instance, this acylation may be obtained by reacting such compound of the general formula (1) where $R_4$ is a hydrogen atom, with an alkanoic acid anhydride or acid chloride in an organic solvent such as aqueous methanol, aqueous dioxane and the like in the presence or absence of an inorganic base such as sodium hydroxide or an organic base such as triethylamine and the like.

The reaction mixture as obtained from the condensation reaction of producing the compound of the formula (1) as above may then be processed in a usual manner for isolation and purification of the desired compound of the formula (1). If necessary, the compound of the general formula (1) may easily be converted in a known manner into the form of an intermolecular salt, free carboxylic acid, free base, a metal salt (carboxylate) such as sodium salt, an acid-addition salt with an inorganic acid such as hydrochloride or a salt with an amine such as dicyclohexylamine.

The compound of the general formula (3) which is used as the starting material in the above-mentioned condensation process may be known ones, and AHPA and p-hydroxyAHPA are described in Japanese patent application prepublication "Kokai" No. 52-136118 and No. 54-79248, respectively (see U.S. Pat. No. 4,189,604).

According to a second aspect of this invention, there is provided a pharmaceutical composition, useful as analgesic agent, which comprises as the active ingredient, a compound of the formula (1) or a compound of the formula (1a) as defined hereinbefore or a pharmaceutically acceptable salt or ester thereof, in combination with a pharmaceutically acceptable carrier for said compound.

According to a third aspect of this invention, there is provided a method of therapeutically treating an animal feeling pain, including humans feeling pain, which comprises administering to the animal, a compound of the formula (1) or a compound of the formula (1a) or a pharmaceutically acceptable salt or ester thereof, in a non-toxic amount sufficient to reduce or eliminate the pain.

According to a fourth aspect of this invention, there is provided a method of enhancing the analgesic activity of morphine when administered to an animal feeling pain, including humans feeling pain, which comprises administering an effective and non-toxic amount of a compound of the formula (1) or the formula (1a) or a pharmaceutically acceptable salt or ester thereof to the animal, just before or at the same time as when morphine is given to the animal for the analgesic purpose.

The pharmaceutical composition of this invention, owing to its analgesic activity, may be utilized for the analgesic or antinociceptive treatment of pain in animals, including men. The composition of this invention may be given orally, parenterally or intrarectally or even intramedullarily or intraspinally e.g. by intralumbar puncture and may be formulated into a suitable form for the route of administration employed. Composition in the form of injectable solution may contain 0.1% to 10.0% by weight of the compound of the formula (1) or (1a) as active ingredient, and also one or more of a pH-adjuster, buffer, stabilizer, local anesthetics and an additive for rendering the solution isotonic. The injectable solution may be prepared to be adapted for subcutaneous, intramuscular or intravenous injection by any conventional pharmaceutical technique. Solid composition for oral administration which may be in the form of tablets, coated tablets, granules, powder and capsules, may contain excipients for the active ingredient, and if required, other additives, including disintegrators, lubricants, colorants, flavors and the like. The proportion of the active compound to the carrier may be at a ratio of 1:1 to 1:100 by weight and may usually be chosen appropriately depending on the form of the orally administrable formulation prepared. The optimal dosage of the compound of the formula (1) or (1a) administered will, of course, depend on the mode of administration, sex, body weight, age, disease conditions of the patients and the treatment aimed. By way of guideline, for men, the unit dosage generally contains from 20 mg to 2 g of the compound of the formula (1) or (1a) which may be given to an adult person one or more times per day.

The high analgesic activity of the compounds of the general formula (1) or the formula (1a) according to this invention are now described with reference to the following experiments. For this purpose, the compounds Nos. 1 to 18 represented by their abbreviations set out in Table 1 were tested in respect of their inhibitory activity against enkephalinase and their effect of enhancing morphine analgesia in rats by the following procedures.

Test 1

Inhibitory activity against enkephalinase were tested.
Testing method:

A preparation of enkephalinase was made by homogenizing corpus striatum of rat brain and by partial purification of the brain homogenate according to the method of Gorenstein et al (see the "Life Science" Vol. 25, 2065~2070 (1979) Pergamon Press, U.S.A.).

A test compound was dissolved in a mixture of Trishydrochloride buffered solution (pH 7.7) and an aqueous 1% Triton X100 (an active surfactant) to such a concentration that the added quantity of the test compound amounted to one-tenth of the volume of said mixture. To the solution of the test compound so prepared was added the enkephalinase, followed by incubation for five minutes at ambient temperature and further by addition of methionine-enkephaline as the substrate. The admixture so obtained was incubated at 37° C. for 1 hour and then subjected to a high-performance liquid chromatography in such a manner that the Tyr-Gly-GLy (a fragment of the methionine-enkephaline) formed by the enzymatic degradation of methionine-enkephaline was isolated in some fractions of the eluate and the quantity of Tyr-Gly-GLy was determined by an electro-chemically analysing detector. In this way, IC$_{50}$ value of the test compound, namely the dose of the test compound required for 50% inhibition of the enkephalinase was measured. The test results are shown in Table 2, column 1 below.

Test 2

Effect of enhancing morphine analgesia was tested.
Test method:

To Wistar rats (10 week-age, male, body weight 250~300 g) was given intraperitoneally morphine at a dose of 0.5 mg/kg, and these rats receiving the morphine were classified into the group of morphine analgesia-effective rats and the group of morphine analgesia-non-effective rats according to the classification method described in the "Showa Igakukai Zasshi" Vol. 39, No. 5, pages 537~542 (1979). The morphine analgesia-non-effective rats so classified were used as the test animal in this test for estimating the activity of the test compound for enhancement of morphine analgesia. After about 1 week was lapsed since the above classification method, the test procedure of estimating the activity of the test compound for enhancement of morphine analgesia was conducted by administering intraperitoneally 250 mg/kg of the test compound of this invention suspended in water containing 5% gum arabic and 1% Tween 80 (an active surfectant) to the test rats and 10 minutes later by intraperitoneally administering 0.5 mg/kg of morphine to these test rats. The effect of analgesia was evaluated according to the method of tail-flick latency of rats described in the "Showa Igakukai Zasshi" Vol. 39, No. 5, pages 537~542 (1979). The evaluation of pain threshold of rats according to the tail-flick latency method was made as follows: Radiant heat stimulus was applied to the region of the rat tail which positioned 1 cm away from the tail tip and which had been colored black with a black-dye, and the time of latency involved in the tail flick, namely the period of time lapsing between the time of application of the heat stimulus and the time of the reflective flick response of the tail was measured. The quantity of the heat applied was so controlled that the average time of latency of the tail-flick response appearing in the control group of rats (receiving neither the test compound nor the morphine) was about 2.0 seconds. The tests were accomplished as long as the maximum value for the tail-flick latency was 7.0 seconds or less, as otherwise the skin of the rat tail could be damaged by the application of heat. In other words, if the time for the tail-flick latency was longer than 7.0 seconds, the tests were stopped to prevent the damage of the rat tail. The radiant heat stimulus was repeated 5 times for each test rat at an interval of 15 minutes and the times of latency in the flick response of the tail measured in each test were averaged. In each test, 5 rats were used.

The difference in the time of the tail-flick latency between the test rats (receiving 250 mg/kg of the test compound plus 0.5 mg/kg of morphine) and the control rats (receiving 0.5 mg/kg of morphine alone) was calculated, and the effect for enhancement of morphine analgesia was estimated in term of the value of percentages which were calculated by the following equation:

$$\text{Percent of enhancement} = \frac{\text{(Test rat)} - \text{(Control rat)}}{\text{(Control rat)}} \times 100$$

The test results obtained are listed in Table 2, column 2 below.

TABLE 2

| Compound No. | Compound Abbreviaiation | Inhibitory activity to enkephalinase IC$_{50}$ (milimol) | Morphine Analgesia enhancement (%) |
|---|---|---|---|
| 10 | D-Phe-AHPA | 0.74 | 35.0 |
| 11 | HABA-AHPA | 1.28 | 21.6 |
| 2 | Gly-AHPA OMe.HCl | 0.30 | 11.6 |
| 3 | N—Ac-Gly-AHPA OMe | 5.48 | 22.9 |
| 4 | GlyGly-AHPA | 0.24 | 10.6 |
| 5 | GlyGly-AHPA OMe.HCl | 1.52 | 19.0 |
| 6 | N—Ac-GlyGly-AHPA | 2.45 | 32.5 |
| 14 | D-Ala-AHPA | 2.14 | 16.8 |
| 16 | TyrGlyGly-(2R,3S)—AHPA | 0.44 | 15.2 |
| 1 | Gly-AHPA | 2.78 | 25.7 |
| 9 | D-Leu-AHPA | 2.48 | 26.3 |
| 8 | L-Leu-AHPA | 2.56 | 22.5 |
| 7 | Sar-AHPA | — | 16.2 |
| 12 | AHPA-AHPA | >20 | 15.7 |
| 15 | N—For-D-Ala-AHPA.Na | 0.15 | 19.7 |
| 13 | N—Ac-GlyGly-AHPA.Na | 2.45 | 33.1 |
| 17 | D-Phe-p-OH-AHPA | 0.13 | 32.1 |
| 18 | D-Leu-(2B,3R)—APHA | 2.65 | 23.4 |
| Comparative Bestatin | | 0.59 | 19.9 |
| Comparative Morphine (0.5 mg/kg) | | — | 0 |
| Comparative Morphine (2 mg/kg) | | — | 28.4 |
| Comparative Morphine (3 mg/kg) | | — | 35.1 |

Note:
The above Compound Nos. and abbreviations are same as those set out in Table 1.

Test 3

Analgesic activity of test compound was estimated according to the acetic acid-writhing method.
Testing procedure:

Mice groups each containing 10 mice of ddy-strain (male, 5 weeks-aged, average body weight about 20 grams) were employed as the test animal. A suspension of the test compound, D-Phe-AHPA suspended in an aqueous solution containing 0.5% of gum arabic and 7% of an active surfectant (consisting of the reaction products of hydrogenated castor oil with polyoxyethylene, commercially available under a registered tradename "Nikkol HCO-60", a product of Nihon Nyukazai Co., Ltd., Japan) was subcutaneously injected into each mouse at a dosage of 30, 150 or 250 mg/kg of the test compound. The above-mentioned suspension so subcutaneously injected was containing the test compound at such a concentration that 0.2 ml of said suspension as injected into each mouse provided the dosage of 30 mg/kg, 150 mg/kg or 250 mg/kg of the test compound. 30 Minutes later, 0.1 mg/10 g of an aqueous solution of 0.6% of acetic acid was injected intraperitoneally into the mice. 5 Minutes after the injection of the aqueous acetic acid, estimation was commenced to count the number of the writhing reaction of the treated mice (the motions such as abdominal constrictions and extensions of the treated mice as induced by the injection of acetic acid) which took place during the subsequent 15 minutes (see the Japanese medical book "Iyaku Kaihatsu Koza" Vol. 5 pages 282~286, published from Chijin-Shokan in 1971 and an English medicinal journal "Brit. J. Pharmacol." 32, pages 295~310, 1968). For control, another mice groups received the subcutaneous administration of an aqueous solution containing no test compound but containing 0.5% of gum arabic and 7% of the active surfactant (Nikkol HCO-60). The rate (%) of suppressing the writhing reactions was evaluated as compared to the control group. "Students-t-test" was employed for the statistical analysis of the test results.

The test results obtained are tabulated in Table 3 below.

It was observed that D-Phe-AHPA suppressed the acetic acid-writhing reaction in the dosage-depending manner, revealing that D-Phe-AHPA alone exhibits the analgesic activity.

TABLE 3

| | Analgesic activity of compound (tested alone) according to the acetic acid-writhing method | | |
| --- | --- | --- | --- |
| Test Compound | Dosage of test compound (mg/kg) | Number of Writhings (Average value ± standard error) | Suppression (%) |
| Control | 0 | 77.1 ± 4.8 | 0 |
| D-Phe-AHPA | 30 | 48.3 ± 3.7*** | 37.4 |
| D-Phe-AHPA | 150 | 43.9 ± 3.8*** | 43.1 |
| D-Phe-AHPA | 250 | 31.3 ± 8.0*** | 59.4 |

***p < 0.001

From the foregoing data, it is clear that the new compounds of this invention exhibit the effect of inhibiting enkephalinase and also the effect of enhancing the morphine analgesia by about 6 times. In a usual analgesic test, it was also observed that the new compounds of this invention show the analgesic activity.

For estimation of acute toxicity of the compounds of the formula (1) according to this invention, Gly-AHPA (Compound No. 1) was tested as a representative example. Thus, when this test compound was orally given at a dose of 2 g/kg to ICR-strain mice (male, 5 week-age, average body weight 20 g, 6 mice in each test group), all of the treated mice survived, revealing that the compounds of the this invention are of a lower toxicity.

From the foregoing, it is clear that the new compounds of this invention are useful as an analgesic or antinociceptive agent of new type when used alone or as an analgesic-aid which is useful to enhance the analgesic activity of morphine when it is administered in association with morphine.

EXAMPLE 1

Synthesis of (2S,3R)-N-glycylamino-2-hydroxy-4-phenylbutanoic acid

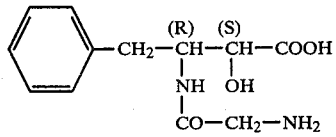

N-Benzyloxycarbonylglycine (1.26 g, 6.0 mM) and (2S,3R)-3-amino-2-hydroxy-4-phenylbutanoic acid benzylester p-toluenesulfonate (2.75 g, 6.0 mM) were admixed with 20 ml of tetrahydrofuran, followed by addition of 0.66 ml (6.0 mM) of N-methylmorpholine and 811 mg of 1-hydroxybenzotriazole. The resulting solution was ice-cooled and then admixed with 1.362 g (6.6 mM) of dicyclohexylcarbodiimide, followed by stirring for 4 hours under ice-cooling. The reaction mixture was filtered to remove the urea derivative as precipitated, and the filtrate was concentrated to dryness under reduced pressure. The solid residue was taken up into 30 ml of ethyl acetate and the solution obtained was washed successively with 10 ml of 1N hydrochloric acid, with 10 ml of distilled water, with 10 ml of 1N aqueous sodium hydroxide and finally with distilled water (10 ml×2). The organic solvent phase was mixed with anhydrous sodium sulfate for drying, and the mixture was filtered to remove the solid mass of sodium sulfate. The solution (the filtrate) was concentrated to dryness under reduced pressure to give a crude product. Crystallization of this product from ethyl acetate-ethylether gave (2S,3R)-3-N-benzyloxycarbonylglycylamino-2-hydroxy-4-phenylbutanoic acid benzylester in a yield of 2.80 g (5.88 mM, 98%).

The compound (2.7 g, 5.67 mM) obtained as above was dissolved in 27 ml of dioxane and the resultant solution was admixed with 9 ml of water and 300 mg of palladium black as the hydrogenolysis catalyst. The mixture was subjected to hydrogenolysis at ambient temperature with hydrogen gas at 3 atm. for 16 hours. The reaction mixture was filtered to remove the catalyst, and the filtrate was concentrated to dryness under reduced pressure. Recrystallization of the residue from methanol gave (2S,3R)-3-glycylamino-2-hydroxy-4-phenylbutanoic acid as crystal, in a yield of 1.13 g (4.48 mM; 74.7%). m.p. 210°~213° C. (dec.). [α]$_D^{25}$+22.5° (c 1.0, 1N-HCl). Mass spectrometry: m/e 253 (M+1).

Elemental Analysis: Found: C 56.95, H 6.43, N 10.89%. Calcd. for $C_{12}H_{16}N_2O_4$ (Molecular weight 252.273): C 57.13, H 6.39, N 11.10%.

EXAMPLE 2

Synthesis of (2S,3R)-N-glycylamino-2-hydroxy-4-phenylbutanoic acid methylester hydrochloride (2S,3R)-3-glycylamino-2-hydroxy-4-phenylbutanoic acid (505 mg, 2.0 mM) as obtained by Example 1 was dissolved in 20 ml of a mixture of 5% aqueous HCl and methanol and allowed to stand overnight at ambient temperature. The reaction mixture was concentrated to dryness to give 630 mg of a crude product. This product was dissolved in 5 ml of distilled water and the solution was passed through a column of 200 ml of Amberlite XT-2 and the column was developed with distilled water for purification. The eluate was concentrated to dryness to give 483 mg of (2S,3R)-3-glycylamino-2-hydroxy-4-phenylbutanoic acid methylester hydrochloride as a white powder. Yield 80%. m.p. 105°~126° C. (dec.). [α]$_D^{25}$+5.0° (c 0.1, 1N-HCl). Mass spectrometry: m/e 267 (M+1).

Elemental analysis Found: C 51.52, H 6.54, N 9.03%. Calcd. for $C_{13}H_{18}N_2O_4$ (Molecular weight 302.760): C 51.57, H 6.33, N 9.25%.

EXAMPLE 3

Synthesis of (2S,3R)-3-N-(N'-acetylglycyl)amino-2-hydroxy-4-phenylbutanoic acid methylester

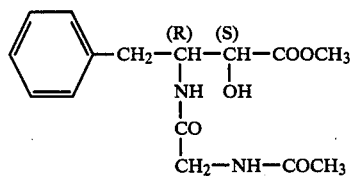

605 mg (2.0 mM) of (2S,3R)-3-N-glycylamino-2-hydroxy-4-phenyl butanoic acid methylester hydrochloride as obtained by Example 2 was dissolved in 10 ml of water, and the solution was passed through a column of 10 ml of Amberlite CG400 (acetate form) and the column was washed with 20 ml of distilled water. The washings and the eluate were combined together and then concentrated to dryness under reduced pressure. The residue was admixed with 10 ml of methanol and 2 ml of acetic anhydride, followed by stirring at ambient temperature for 30 minutes. The reaction solution was concentrated under reduced pressure. The residue was crystallized from a mixture of methanol and water to give 510 mg (1.65 mM) of the above titled product as crystals. Yield 82.5%. m.p. 151°~157° C. (dec.). $[\alpha]_D^{25} - 34°$ (c 1.0, methanol) Mass spectrometry (FD): m/e 308 (M+) and 331 (M+Na)+.

Elemental analysis: Found: C 58.41, H 6.60, N 8.95% Calcd. for $C_{15}H_{20}N_2O_5$ (molecular weight 308.336): C 58.43, H 6.54, N 9.09%.

EXAMPLE 4

Synthesis of (2S,3R)-3-N-glycylglycylamino-2-hydroxy-4-phenylbutanoic acid

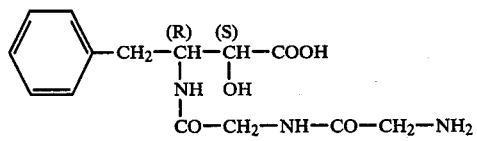

N-Benzyloxycarbonylglycylglycine (1.33 g, 5.0 mM) and (2S,3R)-3-amino-2-hydroxy-4-phenylbutanoic acid benzylester p-toluenesulfonate (2.29 g, 5.0 mM) were reacted with each other in the same manner as in Example 1 to afford 2.51 g (4.7 mM, yield 94%) of the N-protected derivative of (2S,3R)-3-N-glycylglycylamino-2-hydroxy-4-phenylbutanoic acid. This compound was then subjected to the deprotection treatment as in Example 1, and the resultant product was recrystallized from methanol to give 1.18 g (3.81 mM, 76.2%) of the title compound as crystals. m.p. 183°~188° C. (dec.). $[\alpha]_D^{25} - 15°$ (c 1.0, 1N-HCl). Mass spectrometry: m/e 310 (M+1).

Elemental analysis: Found: C 53.98, H 6.30, N 13.29%. Calcd. for $C_{14}H_{19}N_3O_5$ (molecular weight 309.324): C 54.36, H 6.19, N 13.58%.

EXAMPLE 5

Synthesis of (2S,3R)-3-N-glycylglycylamino-2-hydroxy-4-phenylbutanoic acid methylester hydrochloride (2S,3R)-3-N-Glycylglycylamino-2-hydroxy-4-phenylbutanoic acid (619 mg, 2.0 mM) obtained in Example 4 was treated as in Example 2 to afford (2S,3R)-3-N-glycylglycylamino-2-hydroxy-4-phenylbutanoic acid methylester hydrochloride in the form of a colorless powder. Yield 583 mg (1.62 mM; 81%). m.p. 106°~116° C. (dec.). $[\alpha]_D^{25} + 12°$ (c 1.0, 1N-HCl). Mass spectrometry: m/e 324 (M+1).

Elemental analysis: Found: C 49.16, H 6.35, N 11.33%. Calcd. for $C_{15}H_{21}N_3O_5 \cdot HCl$ (molecular weight 359.812): C 50.07, H 6.16, N 11.68%.

EXAMPLE 6

Synthesis of (2S,3R)-3-N-(N'-acetylglycylglycyl)amino-2-hydroxy-4-phenylbutanoic acid

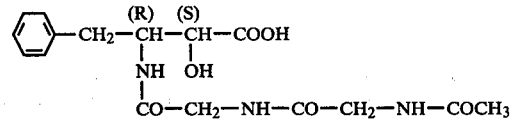

(2S,3R)-3-N-Glycylglycylamino-2-hydroxy-4-phenylbutanoic acid (619 mg, 2.0 mM) obtained in Example 4 was admixed with 10 ml of methanol and 2 ml of acetic anhydride, followed by stirring for 2 hours at ambient temperature. The reaction solution was then concentrated to dryness under reduced pressure. The residue was dissolved in 5 ml of methanol and the resultant solution was chromatographed in a column of 500 ml of Sephadex LH 20 (a product of Sephadex Fine Chemical Co., Sweden) and developed with methanol. The fractions of the eluate containing the desired compound were concentrated to dryness and the residue was recrystallized from water to give 561 mg (1.6 mM, yield 80%) of the above titled compounds as crystals. m.p. 114°~132° C. (dec.). $[\alpha]_D^{25} - 47°$ (c 1.0, 0.1N-NaOH). Mass spectrometry (FD): m/e 352 (M+1)+ and 374 (M+Na)+.

Elemental analysis: Found: C 54.55, H 6.13, N 11.72%. Calcd. for $C_{16}H_{21}N_3O_5$ (molecular weight 351.361): C 54.70, H 6.02, N 11.96%.

EXAMPLE 7

Synthesis of (2S,3R)-3-N-(N'-methylglycyl)amino-2-hydroxy-4-phenylbutanoic acid (Sar-AHPA)

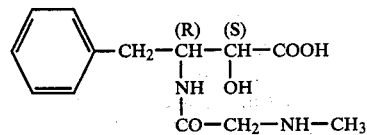

N-Benzyloxycarbonyl-N-methylglycine (2.23 g, 10 mM) and (2S,3R)-3-amino-2-hydroxy-4-phenylbutanoic acid benzylester p-toluenesulfonate (4.58 g, 10 mM) were reacted with each other in the same manner as in Example 1 to afford 4.36 g (8.99 mM, yield 88.9%) of the N-protected derivative of (2S,3R)-3-N-(N'-methylglycyl)amino-2-hydroxy-4-phenylbutanoic acid as a powder. This N-protected product was then subjected to the deprotection treatment as in Example 1 and the resultant product was recrystallized from methanol to give 1.9 g (7.14 mM, yield 71.4%) of the above titled compound as crystal. m.p. 240°~244° C. $[\alpha]_D^{25}+33°$ (c 1.0, 1N-HCl). Mass spectrometry: m/e 267 (M+1)$^+$.

Elemental analysis: Found: C 58.33, H 6.89, N 10.37%. Calcd. for $C_{13}H_{18}N_2O_4$ (molecular weight 266.299): C 58.64, H 6.81, N 10.52%.

EXAMPLE 8

Synthesis of (2S,3R)-3-N-(S)-leucylamino-2-hydroxy-4-phenyl-butanoic acid

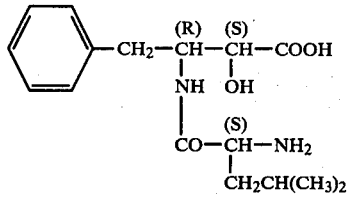

N-Benzyloxycarbonyl-(S)-leucine (2.65 g, 10 mM) and (2S,3R)-3-amino-2-hydroxy-4-phenylbutanoic acid benzylester p-toluenesulfonate (4.58 g, 10 mM) were reacted with each other in the same manner as in Example 1 to 4.85 g (9.1 mM, yield 91%) of the N-protected derivative of (2S,3R)-3-N-(S)-leucylamino-2-hydroxy-4-phenylbutanoic acid. This N-protected product was then subjected to the deprotection treatment as in Example 1 to afford 2.43 g (7.89 mM, yield 78.9%) of the above titled compound as crystals. m.p. 207°~210° C. (dec.). $[\alpha]_d^{25}-3°$ (c 1.0, 1N-HCl). Mass spectrometry: m/e 309 (M+1)$^+$.

Elemental analysis: Found: C 62.15, H 7.83, N 8.87%. Calcd. for $C_{16}H_{24}N_2O_4$ (molecular weight 308.380): C 62.32, H 7.84, N 9.08%.

EXAMPLE 9

Synthesis of (2S,3R)-3-N-(R)-leucylamino-2-hydroxy-4-phenyl-butanoic acid

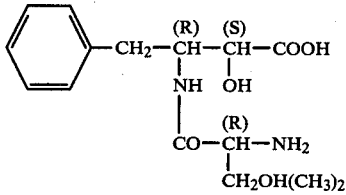

N-Benzyloxycarbonyl-(R)-leucine (1.33 g, 5 mM) and (2S,3R)-3-amino-2-hydroxy-4-phenylbutanoic acid benzylester p-toluenesulfonate (2.29 g, 5 mM) were reacted with each other in the same manner as in Example 1 to give 2.33 g (4.37 mM, 87.4%) of the N-protected derivative of (2S,3R)-3-N-(R)-leucylamino-2-hydroxy-4-phenylbutanoic acid. This N-protected product was then subjected to the deprotection treatment as in Example 1 to afford 1.15 g (3.73 mM, 74.6%) of the above titled compound as crystals. m.p. 184°~189° C. (dec.). $[\alpha]_D^{25}+40°$ (c 1.0, 1N-HCl). Mass spectrometry: m/e 309 (M+1)$^+$.

Elemental analysis: Found: C 62.03, H 7.92, N 8.75%. Calcd. for $C_{16}H_{24}N_2O_4$ (molecular weight 308.380): C 62.32, H 7.84, N 9.08%.

EXAMPLE 10

Synthesis of (2S,3R)-3-N-((R)-phenylalanyl)amino-2-hydroxy-4-phenylbutanoic acid

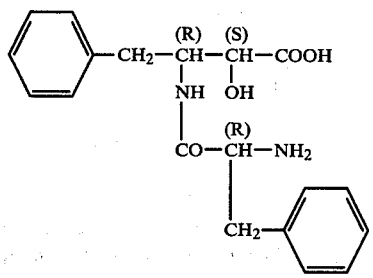

N-Benzyloxycarbonyl-(R)-phenylalanine (2.99 g, 10 mM) and (2S,3R)-3-amino-2-hydroxy-4-phenylbutanoic acid benzylester p-toluenesulfonate (4.58 g, 10 mM) were reacted with each other in the same manner as in Example 1 to give 5.31 g (9.37 mM) of the N-protected derivative of (2S,3R)-3-N-((R)-phenylalanyl)amino-2-hydroxy-4-phenylbutanoic acid. This N-protected product was then subjected to the deprotection treatment as in Example 1 to afford 2.82 g (8.24 mM, 82.4%) of the above titled compound as crystals. m.p. 178°~182° C. (dec.). $[\alpha]_D^{25}+63°$ (c 1.0, 1N-HCl). Mass spectrometry: m/e 343 (M+1)$^+$.

Elemental analysis: Found: C 66.38, H 6.37, N 8.01%. Calcd. for $C_{19}H_{22}N_2O_4$ (molecular weight 342.398): C 66.65, H 6.48, N 8.18%.

EXAMPLE 11

Synthesis of (2S,3R)-3-N-[4'-amino-(2'S)-2'-hydroxybutanoyl]amino-2-hydroxy-4-phenylbutanoic acid [HABA-AHPA]

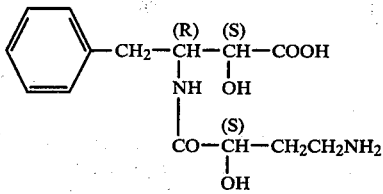

(S)-4-N-Benzyloxycarbonylamino-2-hydroxybutanoic acid (2.53 g, 10 mM) and (2S,3R)-3-amino-2-hydroxy-4-phenylbutanoic acid benzylester p-toluenesulfonate (4.58 g, 10 mM) were reacted with each other in the same manner as in Example 1 to give 4.75 g (9.12 mM, 91.2%) of the N-protected derivative of (2S,3R)-3-N-[4'-amino-(2'S)-2'-hydroxy-butanoyl] amino-2-hydroxy-4-phenylbutanoic acid. This N-protected product was then subjected to the deprotection treatment as in Example 1 to afford 2.24 g (7.56 mM, 75.6%) of the titled compound as crystals. m.p. 108~128° C. (dec.). $[\alpha]_D^{25}-20°$ (c 1.0, 1N-HCl). Mass spectrometry: m/e 297 (M+1)$^+$.

Elemental analysis: Found: C 56.28, H 6.96, N 9.11%. Calcd. for $C_{14}H_{20}N_2O_5$ (molecular weight 296.325): C 56.75, H 6.80, N 9.45%.

EXAMPLE 12

Synthesis of (2S,3R)-3-N-[(2'S,3'R)-3'-amino-2'-hydroxy-4'-phenyl-butanoyl]amino-2-hydroxy-4-phenylbutanoic acid (AHPA-AHPA)

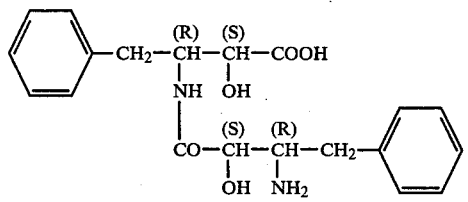

(2S,3R)-3N-Benzyloxycarbonylamino-2-hydroxy-4-phenylbutanoic acid (3.29 g, 10 mM) and (2S,3R)-3-amino-2-hydroxy-4-phenylbutanoic acid benzylester p-toluenesulfonate (4.58 g, 10 mM) were reacted with each other in the same manner as in Example 1 to give 5.38 g (9.02 mM, 90.2%) of the N-protected derivative of (2S,3R)-3-N-[(2'S,3'R)-3'-amino-2'-hydroxy-4'-phenylbutanoyl]amino-2-hydroxy-4-phenylbutanoic acid. This N-protected product was then subjected to the deprotection treatment as in Example 1 to afford 2.63 g (7.06 mM, 70.6%) of the titled compound as crystals. m.p. 221°~235° C. (dec.). $[\alpha]_D^{25} -41°$ (c 1.0, 1N-HCl). Mass spectrometry: m/e 373 (M+1)+.

Elemental analysis: Found: C 64.15, H 6.39, N 7.18%. Calcd. for $C_{20}H_{24}N_2O_5$ (molecular weight 372.424): C 64.50, H 6.50, N 7.52%.

EXAMPLE 13

Synthesis of (2S,3R)-3-N-(N'-acetylglycylglycyl)amino-2-hydroxy-4-phenylbutanoic acid sodium salt (2S,3R)-3-N-(N'-Acetylglycylglycyl) amino-2-hydroxy-4-phenylbutanoic acid (176 mg, 0.5 mM) obtained in Example 6 was suspended in 5 ml of distilled water, and 1N aqueous sodium hydroxide was added to the suspension until pH became 8.0 so that the acid dissolved in water. The resultant aqueous solution was passed through a column of 70 ml of Amberlite XT-2, and the column was developed with water. The eluate was collected in 10 ml-fractions and each fraction was examined by silica gel thin layer chromatography for presence of the aimed product. The combined fractions Nos. 9 to 20 were concentrated under reduced pressure and freeze-dried to afford 157 mg (0.42 mM, 84%) of a white powder of the titled compound. m.p. 272~277 (dec.). An aqueous solution of 10 mg of the sodium salt product per ml of water showed pH 7.6. $[\alpha]_D^{25} -45°$ (c 1.0, 0.1N-NaOH).

Elemental analysis: Found: C 50.96, H 5.59, N 10.93%. Calcd. for $C_{16}H_{20}N_3O_6Na$ (molecular weight 373.343): C 51.47, H 5.40, N 11.26%.

EXAMPLE 14

Synthesis of (2S,3R)-3-N-((R)-alanyl) amino-2-hydroxy-4-phenylbutanoic acid

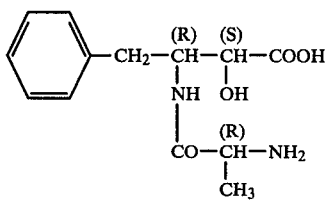

N-Benzyloxycarbonyl-(R)-alanine (941 mg), (2S,3R)-3-amino-2-hydroxy-4-phenylbutanoic acid benzylester p-toluenesulfonate (1.879 g), N-methylmorpholine (0.464 ml) and N-hydroxybenzotriazol (627 mg) were dissolved in 8 ml of tetrahydrofuran. The solution obtained was mixed with 958 mg of dicyclohexylcarbodiimide and processed in the same manner as in Example 1. The resultant N-protected derivative of (2S,3R)-3-N-((R)-alanyl)amino-2-hydroxy-4-phenylbutanoic acid was purified by a column chromatography on silica gel (50 g of an absorbent, "Mallinckrodt CC-7", developed with chloroform) to give a pure product (1.88 g). Mass spectrometry of this N-protected product gave m/e 491 (M+1). The N-protected product obtained was subjected to the deprotection treatment as in Example 1, and the deprotected product was crystallized from methanol to afford 786 mg of the titled compound as needle-like crystals, m.p. 215°~230° C. (decomposed with discoloration). Mass spectrometry: m/e 267 (M+1). $[\alpha]_D^{25} +75.4°$ (c 1.0, acetic acid)

Elemental analysis: Found: C 58.62, H 6.83, N 10.52%. Calcd. for $C_{13}H_{18}N_2O_4$ (molecular weight 266.33): C 58.94, H 6.35, N 10.62%.

EXAMPLE 15

Synthesis of (2S,3R)-3-N-(N'-formyl-(R)-alanyl) amino-2-hydroxy-4-phenylbutanoic acid sodium salt 53.3 mg of (2S,3R)-3-N-(R)-alanylamino-2-hydroxy-4-phenylbutanoic acid obtained in Example 14 was dissolved in 0.4 ml of 98% aqueous formic acid, and to the resultant solution was added dropwise 0.14 ml of acetic anhydride over 30 minutes under ice-cooling. The reaction was effected for 15 minutes under ice-cooling and the reaction was further continued for two days under ice-cooling. Even after this, it was found that a small amount of the starting material still remained in the reaction solution, in addition to the desired product. The reaction solution was then concentrated to dryness, and then 1 ml of water was added to the residue to redissolve the latter. this procedure of concentration and redissolution was repeated three times. The final residue was admixed with 3 ml of acetone and 1 ml of ethyl acetate, and the mixture was filtered to remove the insoluble starting material. The filtrate was concentrated to dryness to give 47 mg of a white powder. Mass spectrometry of this product gave m/e 295 (M+1).

The product obtained as above was dissolved in 2 ml of water and 1.25 mg of sodium bicarbonate was added to the solution to adjust the pH to 7.8. This solution was passed through a column of 150 mg (0.5 ml) of a nonionic adsorbent resin, "Diaion" HP-20 and the column developed with water, then with water-methanol (10:1), further with water-methanol (5:1) and finally with water-methanol (3:1). The fractions of the eluate from the development with the water-methanol (3:1) were concentrated to afford 25 mg of the above titled desired compound as colorless needles. m.p. 185°~189° C. (dec.). $[\alpha]_D^{25} +91.2°$ (c 1.0, water).

Elemental analysis: Found: C 52.26, H 5.42, N 8.62%. Calcd. for $C_{14}H_{18}N_2O_5Na$ (molecular weight 317.33): C 52.99, H 5.73, N 8.83, Na 7.24%.

EXAMPLE 16

Synthesis of (2R,3R)-3-N-((R)-leucyl)amino-2-hydroxy-4-phenyl-butanoic acid

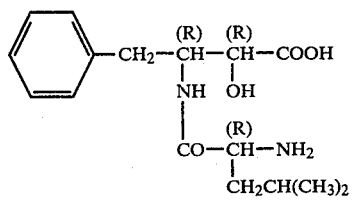

N-Benzyloxycarbonyl-(R)-leucine (210 mg), (2R,3R)-3-amino-2-hydroxy-4-phenylbutanoic acid benzylester p-toluenesulfonate (330 mg), N-methylmorpholine (0.087 mg) and N-hydroxybenzotriazol (98 mg) were dissolved in 2.5 ml of tetrahydrofuran, followed by addition of 164 mg of dicyclohexylcarbodiimide under ice-cooling. The reaction was carried out in the same manner as in Example 1 under stirring to yield the N-protected derivative of the titled compound which was then recrystallized from ethyl acetate to give 341 mg of the N-protected product as crystals. Mass spectrometry of this N-protected product gave m/e 532 (M+1). The N-deprotecting reaction of this compound was carried out in the same manner as in Example 1 to give 109 mg of the titled compound. m.p. 225°~229° C. (dec.). $[\alpha]_D -9.0°$ (c 1.0, acetic acid). Mass spectrometry: m/e 309 (M+1).

Elementary analysis: Found: C 62.32, H 7.84, N 9.08%. Calcd. for $C_{16}H_{24}N_2O_4$ (molecular weight 308.42): C 61.51, H 8.03, N 8.43%.

EXAMPLE 17

Synthesis of (2R,3S)-3-N-((S)-tyrosylglycidylglycyl)amino-2-hydroxy-4-phenylbutanoic acid

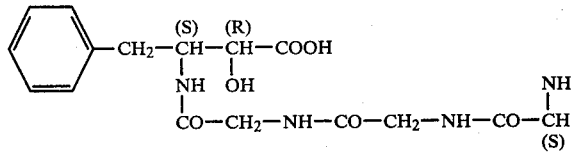

(S)-Tyrosylglycylglycine (100 mg, 0.34 mM) was dissolved in a mixture of 0.08 ml of triethylamine and 0.22 ml of water and the resultant solution was admixed with 0.18 g (0.37 mM) of benzyl 4,6-dimethylpyrimidyl-2-thiol carbonate (a reagent for introduction of benzyloxycarbonyl group as the amino-protecting group) dissolved in 0.22 ml of dioxane, followed by reaction at ambient temperature for 10 hours. The reaction mixture was treated according to the known method as disclosed in "Bulletein of the Chemical Society of Japan", 46, 1269 (1973). The resultant agar-like solid mass was admixed with 1 ml of ethanol and 1 ml of benzene, and the precipitate was formed was separated from the supernatant by decantation. The supernatant contained 70 mg of N,O-bisbenzyloxycarbonyl-(S)-tyrosylglycylglycine and the precipitate comprised 78 mg of N-benzyloxycarbonyl-(S)-tyrosylglycylglycine.

To the latter were added 83 mg of (2R,3S)-AHPA benzylester p-toluenesulfonate, 0.024 ml of N-methylmorpholine and 25 ml of N-hydroxybenzotriazol, and the whole admixture was then dissolved in 2 ml of tetrahydrofuran. The solution obtained was ice-cooled and then admixed with 41 mg of dicyclohexylcarbodiimide. The reaction was continued for 2 days under ice-cooling. The reaction mixture was then processed in the same manner as in Example 1 to give 117 mg of the N-protected derivative of the titled compound as a powder. Mass spectrometry of this N-protected product gave m/e 697 (M+1). The product was subjected to hydrogenolysis as described in Example 1 to effect the N-deprotection, and the reaction solution was concentrated to dryness. The residue was recrystallized from a mixed solvent of water and methanol to afford 32 mg of the titled compound as clorless solid. m.p. 169°~171° C. (dec.). $[\alpha]_D^{25} -13.0°$ (c 1.0, acetic acid). Mass spectrometry: m/e 473 (M+1).

Elemental analysis: Found: C 58.01, H 5.96, N 12.22%. Calcd. for $C_{23}H_{28}N_4O_7$ (molecular weight 472.55): C 58.46, H 5.98, N 11.86%.

EXAMPLE 18

Synthesis of (2S,3R)-3-N-((R)-phenylalanyl)amino-4-p-hydroxyphenylbutanoic acid

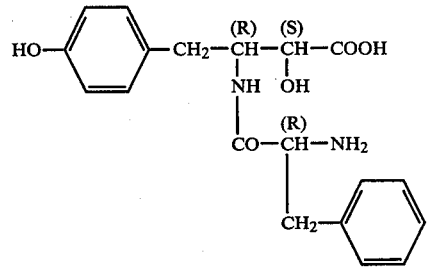

N-Benzyloxycarbonyl-(R)-phenylalanine (1.495 g) and (2S,3R)-3-amino-2-hydroxy-4-p-hydroxyphenyl-butanoic acid benzylester p-toluenesulfonate (2.368 g) were reacted with each other in the same manner as in Example 1 to obtain 2.63 g of the N-protected derivative of the title compound in the form of a colorless powder. This N-protected product was subjected to the hydrogenolysis in the same manner as in Example 1 for the N-deprotection. The reaction products as obtained were sparingly soluble in the mixture of water and dioxane and hence were dissolved in 4.3 ml of 1N-HCl at pH 1.5, followed by filtration of the resultant solution to remove the hydrogenolysis catalyst therefrom. The resulting solution (the filtrate) was neutralized to pH 7 by addition of concentrated aqueous ammonia and subsequently concentrated to a volume of about 3 ml. The product as precipitated was removed by filtration and washed with water, then with ethanol and finally with ethyl ether to give 1.32 g of the above titled desired compound. m.p. 175°~180° C. (dec.). Mass spectrometry: m/e 359 (M+1).

Elemental analysis: Found: C 63.15, H 6.56, N 7.41%. Calcd. for $C_{19}H_{22}N_2O_5$ (molecular weight 358.43): C 63.66, H 6.20, N 7.82%.

In a silica gel thin layer chromatography on silica gel (as TLC plate of "ART 5715", a product of Merck Co., Germany) developed with n-butyl acetate-n-butanol-acetic acid-water (4:4:1:1), the above titled compound obtained gave a single spot at Rf 0.47.

What we claim is:

1. An N-acyl 3-amino-2-hydroxy-4-phenylbutanoic acid of the formula:

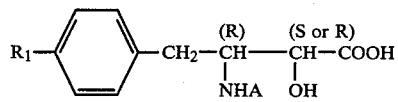
(1a)

wherein $R_1$ is a hydrogen atom or a hydroxyl group; and A is a glycyl group, an N-acetylglycyl group, a methylglycyl group, an R-alanyl group, an R-phenylalanyl group, an N-formyl-R-alanyl group, an R-leucyl group, an S-leucyl group, a glycylglycyl group, an N-acetylglycylglycyl group, an S-tyrosylglycylglycyl group, a 4-amino-(2S)-2-hydroxybutanoyl group or a (2S,3R)-3-amino-2-hydroxy-4-phenylbutanoyl group, or a pharmaceutically acceptable alkyl ester or a pharmaceutically acceptable salt thereof.

2. (2S,3R)-3-N-(R)-Phenylalanylamino-2-hydroxy-4-phenylbutanoic acid.

3. A compound as claimed in claim 1 which is selected from the following:
(2S,3R)-3-N-glycylamino-2-hydroxy-4-phenylbutanoic acid,
(2S,3R)-3-N-glycylamino-2-hydroxy-4-phenylbutanoic acid methyl ester hydrochloride,
(2S,3R)-3-N-(N'-acetylglycyl)amino-2-hydroxy-4-phenylbutanoic acid methyl ester,
(2S,3R)-3-N-glycylglycylamino-2-hydroxy-4-phenylbutanoic acid,
(2S,3R)-3-N-glycylglycylamino-2-hydroxy-4-phenylbutanoic acid methyl ester hydrochloride,
(2S,3R)-3-N-(N'-methylglycyl)amino-2-hydroxy-4-phenylbutanoic acid,
(2S,3R)-3-N-(S)-leucylamino-2-hydroxy-4-phenylbutanoic acid,
(2S,3R)-3-N-(R)-leucylamino-2-hydroxy-4-phenylbutanoic acid,
(2S,3R)-3-N-[4'-amino-(2'S)-2'-hydroxybutanoyl]amino-2-hydroxy-4-phenylbutanoic acid,
(2S,3R)-3-N-[(2'S,3'R)-3'-amino-2'-hydroxy-4'-phenylbutanoyl]amino-2-hydroxy-4-phenylbutanoic acid,
(2S,3R)-3-N-(R)-alanylamino-2-hydroxy-4-phenylbutanoic acid,
(2S,3R)-3-N-(N'-formyl-(R)-alanyl)amino-2-hydroxy-4-phenylbutanoic acid sodium salt,
(2R,3S)-3-N-(S)-tyrosylglycylglycylamino-2-hydroxy-4-phenylbutanoic acid,
(2R,3R)-3-N-(R)-leucylamino-2-hydroxy-4-phenylbutanoic acid.

4. An analgesic composition which comprises as the active ingredient a compound of the formula (1a) as claimed in claim 1 or a pharmaceutically acceptable salt or ester thereof, in combination with a pharmaceutically acceptable carrier for said compound.

5. A method of therapeutically treating an animal feeling pain, including humans feeling pain, which comprises administering to the animal, a compound of the formula (1a) as claimed in claim 1 or a pharmaceutically acceptable salt or ester thereof, in a non-toxic amount sufficient to reduce or eliminate the pain.

6. A method of enhancing the analgesic activity of morphine when administered to an animal feeling pain, including humans feeling pain, which comprises administering an effective and non-toxic amount of a compound of the formula (1a) as claimed in claim 1 or a pharmaceutically acceptable salt or ester thereof to the animal, just before or at the same time as when morphine is given to the animal for the analgesic purpose.

7. (2S-3R)-3-N-(N'-acetylglycylglycyl)amino-2-hydroxy-4-phenylbutanoic acid.

8. (2S-3R)-3-N-(N'-acetylglycylglycyl)amino-2-hydroxy-4-phenylbutanoic acid sodium salt.

9. (2S,3R)-3-N-(R)-phenylalanylamino-2-hydroxy-4-p-hydroxyphenylbutanoic acid.

* * * * *